(12) United States Patent
Liversidge

(10) Patent No.: US 9,783,328 B2
(45) Date of Patent: Oct. 10, 2017

(54) TRAY FOR HANDLING SYRINGE BARRELS

(71) Applicant: Barry Peter Liversidge, Colchester (GB)

(72) Inventor: Barry Peter Liversidge, Colchester (GB)

(73) Assignee: TIP-TOP.COM LTD (GB)

( * ) Notice: Subject to any disclaimer, the term of this patent is extended or adjusted under 35 U.S.C. 154(b) by 0 days.

(21) Appl. No.: 14/521,992

(22) Filed: Oct. 23, 2014

(65) Prior Publication Data

US 2015/0041349 A1    Feb. 12, 2015

Related U.S. Application Data

(63) Continuation of application No. 14/141,183, filed on Dec. 26, 2013, now abandoned, which is a (Continued)

(30) Foreign Application Priority Data

Mar. 12, 2010   (GB) .................................. 1004102.8

(51) Int. Cl.
    *B65B 5/06*        (2006.01)
    *A61M 5/00*        (2006.01)
    (Continued)

(52) U.S. Cl.
    CPC .......... *B65B 5/068* (2013.01); *A61B 19/0256* (2013.01); *A61B 19/0271* (2013.01);
    (Continued)

(58) Field of Classification Search
    CPC ........ A61M 5/008; A61M 5/00; A61M 5/002; A61M 5/00831; A61M 5/32; A61M 5/34;
    (Continued)

(56) References Cited

U.S. PATENT DOCUMENTS 2,523,877 A * 9/1950 Pestolesi ..................... 206/366
2,854,975 A * 10/1958 Cohen ................... A61M 5/315
                                                          604/227

(Continued)

FOREIGN PATENT DOCUMENTS

EP    1138390    10/2001
EP    1449551    8/2004
(Continued)

OTHER PUBLICATIONS

International Search Report, PCT International Application No. PCT/GB2011/050498, mailed Jul. 5, 2011.

*Primary Examiner* — Bryon Gehman
(74) *Attorney, Agent, or Firm* — Grossman Tucker Perreault & Pleger PLLC

(57) ABSTRACT

A handling system for use in the manufacture of syringe barrels includes a tray having an array of apertures with a tubular upstand around each aperture, each upstand at the upper end thereof defining a support surface for a syringe barrel. Each syringe barrel comprises a cylindrical part and an enlargement at or adjacent the rear end of the barrel and carries at its forward end a safe needle device or a needle shield of a greater diameter than the syringe barrel. At least one of the enlargement of the syringe barrel or the support surface has a profile tapering or rounded inwardly in the downward direction so that when the tray is supported generally horizontally and a syringe barrel is lowered into an upstand, the syringe barrel is centered by co-operation between the enlargement and the support surface. The enlargement may be a flange at the rear end of the syringe barrel or could be a further component fitted to the barrel.

23 Claims, 14 Drawing Sheets

Related U.S. Application Data continuation of application No. 13/634,074, filed as application No. PCT/GB2011/050498 on Mar. 14, 2011, now abandoned.

(51) Int. Cl.

| | | |
|---|---|---|
| *B01L 9/00* | (2006.01) | |
| *B65D 25/10* | (2006.01) | |
| *A61J 1/00* | (2006.01) | |
| *B65D 25/34* | (2006.01) | |
| *A61B 19/02* | (2006.01) | |
| *A61B 50/20* | (2016.01) | |
| *A61B 50/30* | (2016.01) | |
| *A61M 5/31* | (2006.01) | |
| *B01L 3/02* | (2006.01) | |
| *A61B 50/00* | (2016.01) | |
| *A61M 5/32* | (2006.01) | |
| *A61B 50/33* | (2016.01) | |

(52) U.S. Cl.
CPC .............. *A61B 50/20* (2016.02); *A61B 50/30* (2016.02); *A61J 1/00* (2013.01); *A61M 5/002* (2013.01); *A61M 5/008* (2013.01); *B01L 9/54* (2013.01); *B65D 25/108* (2013.01); *B65D 25/34* (2013.01); *A61B 50/33* (2016.02); *A61B 2019/0219* (2013.01); *A61B 2050/0065* (2016.02); *A61M 5/3135* (2013.01); *A61M 5/3202* (2013.01); *A61M 2207/10* (2013.01); *B01L 3/0217* (2013.01); *B01L 2200/025* (2013.01)

(58) Field of Classification Search
CPC ...... B65D 25/108; B65D 25/10; A61B 19/02; A61L 2/20; A61L 2/26
USPC ............... 206/364, 366, 348; 604/187, 192
See application file for complete search history.

(56) References Cited

U.S. PATENT DOCUMENTS

| | | | | |
|---|---|---|---|---|
| 4,919,264 | A * | 4/1990 | Shinall .......................... | 206/210 |
| 5,129,886 | A * | 7/1992 | Sincock ........................ | 604/192 |
| 5,372,252 | A * | 12/1994 | Alexander .................... | 206/210 |
| 5,419,775 | A * | 5/1995 | Haffner et al. ............... | 604/227 |
| 5,667,495 | A | 9/1997 | Bitdinger et al. | |
| 6,012,595 | A * | 1/2000 | Thilly .......................... | 211/60.1 |
| 6,019,225 | A * | 2/2000 | Kalmakis et al. ............ | 206/563 |
| 6,149,872 | A * | 11/2000 | Mack et al. .................. | 422/554 |
| 6,719,141 | B2 * | 4/2004 | Heinz et al. ................. | 206/563 |
| 6,846,302 | B2 * | 1/2005 | Shemesh ............... A61M 5/326 | |
| | | | | 128/919 |
| 7,169,361 | B2 * | 1/2007 | Arnold et al. ................ | 422/526 |
| 7,191,904 | B2 * | 3/2007 | Wescott, III ................. | 211/74 |
| 7,258,240 | B2 * | 8/2007 | Wescott, III .................. | 211/74 |
| 7,428,807 | B2 * | 9/2008 | Vander Bush et al. ........ | 53/425 |
| 7,431,157 | B2 * | 10/2008 | Porret et al. .................. | 206/439 |
| 8,100,263 | B2 * | 1/2012 | Vanderbush et al. ...... | 206/524.8 |
| 8,286,791 | B2 * | 10/2012 | Finke ........................... | 206/366 |
| 8,337,468 | B1 * | 12/2012 | Reis .................... A61M 5/3257 | |
| | | | | 604/181 |
| 8,453,838 | B2 * | 6/2013 | Hill ....................... A61M 5/008 | |
| | | | | 211/74 |
| 8,485,357 | B2 * | 7/2013 | Song et al. ................... | 206/366 |
| 8,490,790 | B2 * | 7/2013 | Cocheteux et al. .......... | 206/366 |
| 8,597,255 | B2 * | 12/2013 | Emmott .............. A61M 5/002 | |
| | | | | 604/110 |
| 2008/0244923 | A1 * | 10/2008 | Yarborough et al. ........... | 34/287 |
| 2009/0004063 | A1 * | 1/2009 | Higashihara et al. ........... | 422/99 |
| 2012/0118777 | A1 * | 5/2012 | Kakiuchi et al. ............ | 206/366 |
| 2012/0118903 | A1 * | 5/2012 | Norton ................. B01L 3/0293 | |
| | | | | 220/755 |
| 2012/0193256 | A1 * | 8/2012 | Gagnieux et al. ........... | 206/366 |
| 2012/0234710 | A1 * | 9/2012 | Finke et al. .................. | 206/366 |
| 2013/0186793 | A1 * | 7/2013 | Gagnieux et al. ........... | 206/364 |
| 2013/0296791 | A1 * | 11/2013 | Segev ................. A61M 5/3202 | |
| | | | | 604/173 |

FOREIGN PATENT DOCUMENTS

| | | |
|---|---|---|
| FR | 2498933 | 8/1982 |
| WO | 9218187 | 10/1992 |

\* cited by examiner

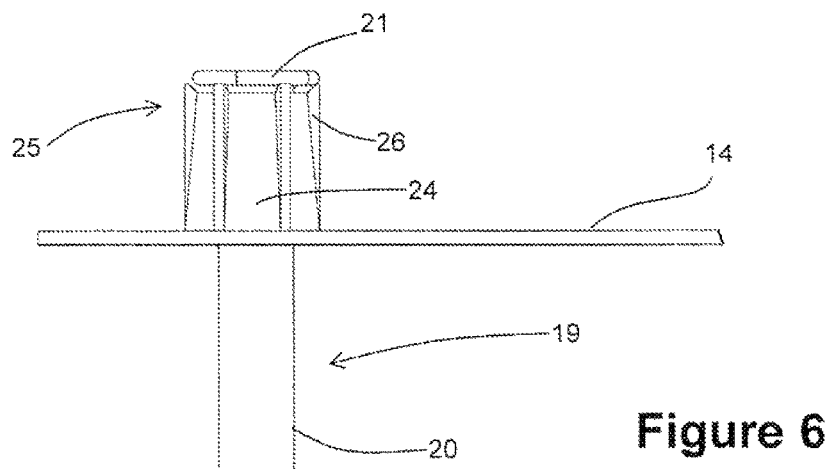
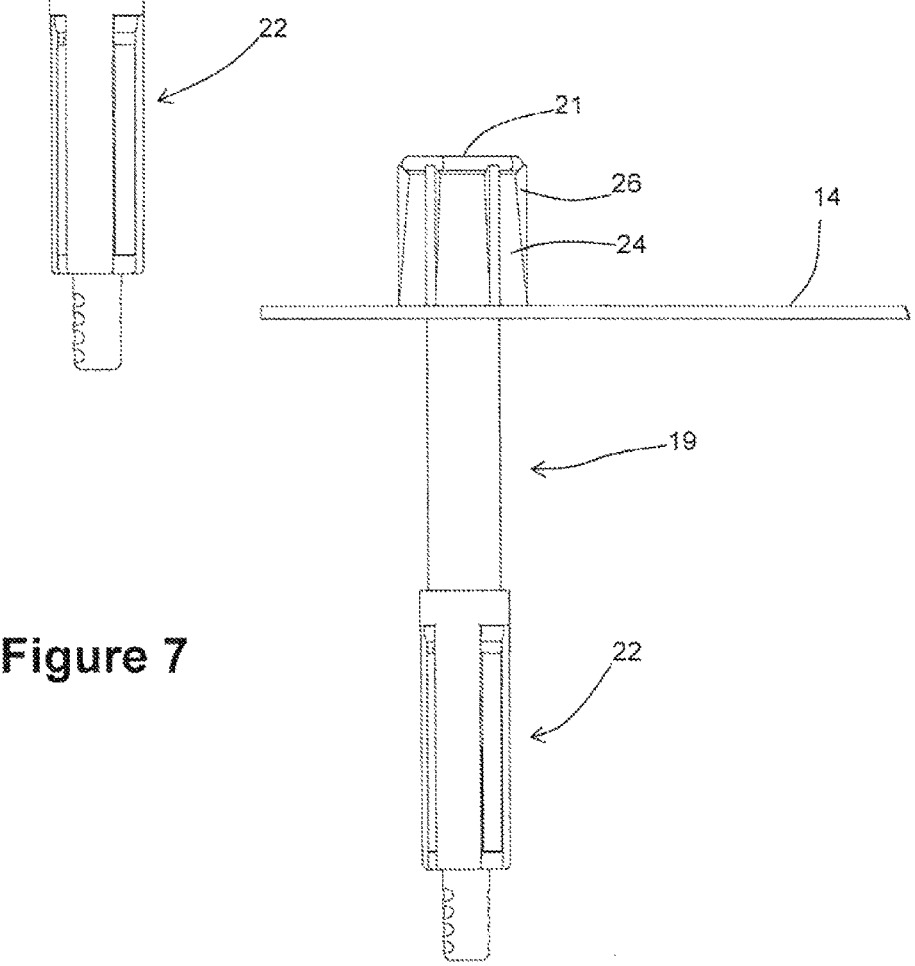
Figure 6
Figure 7

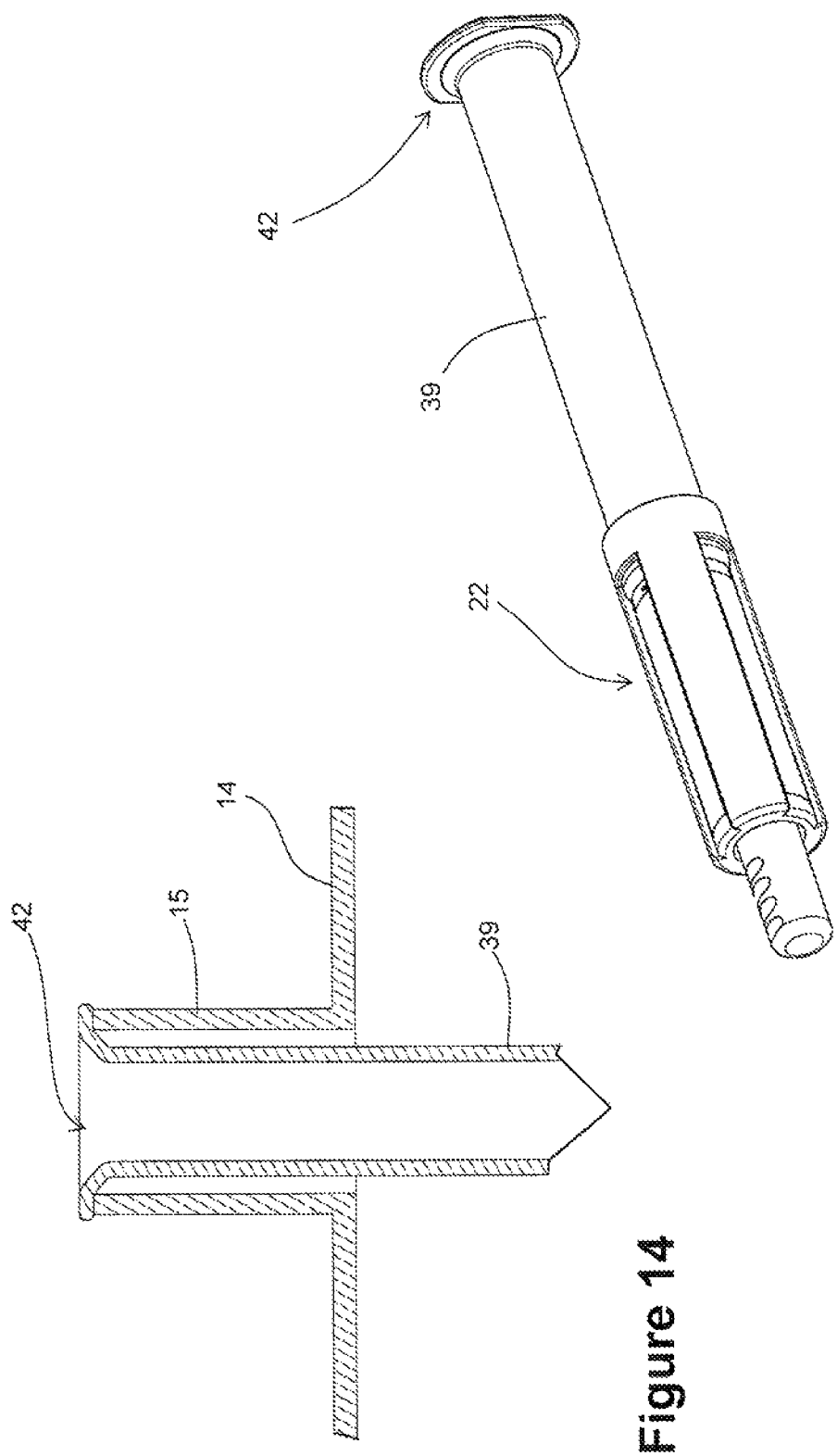

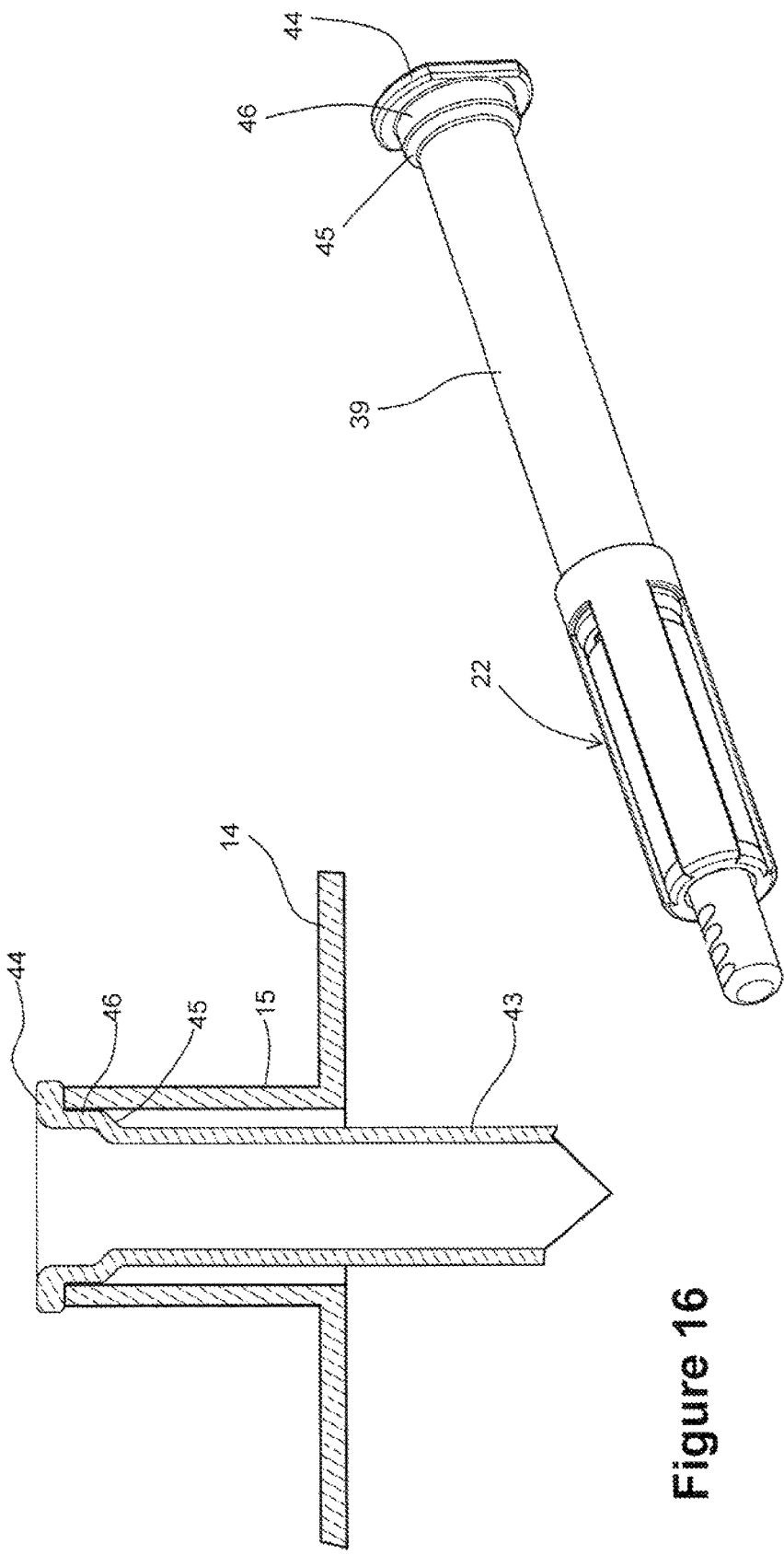

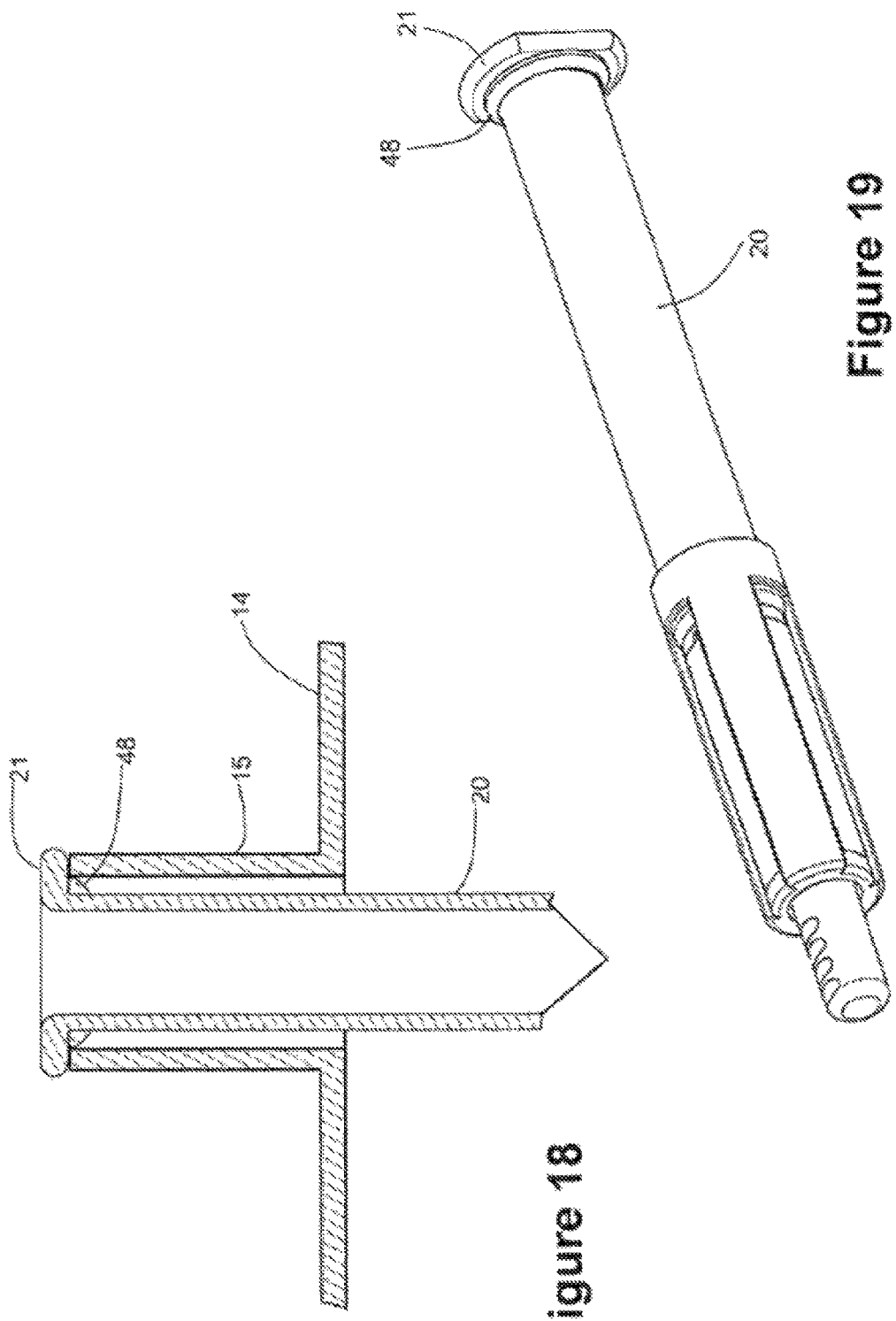

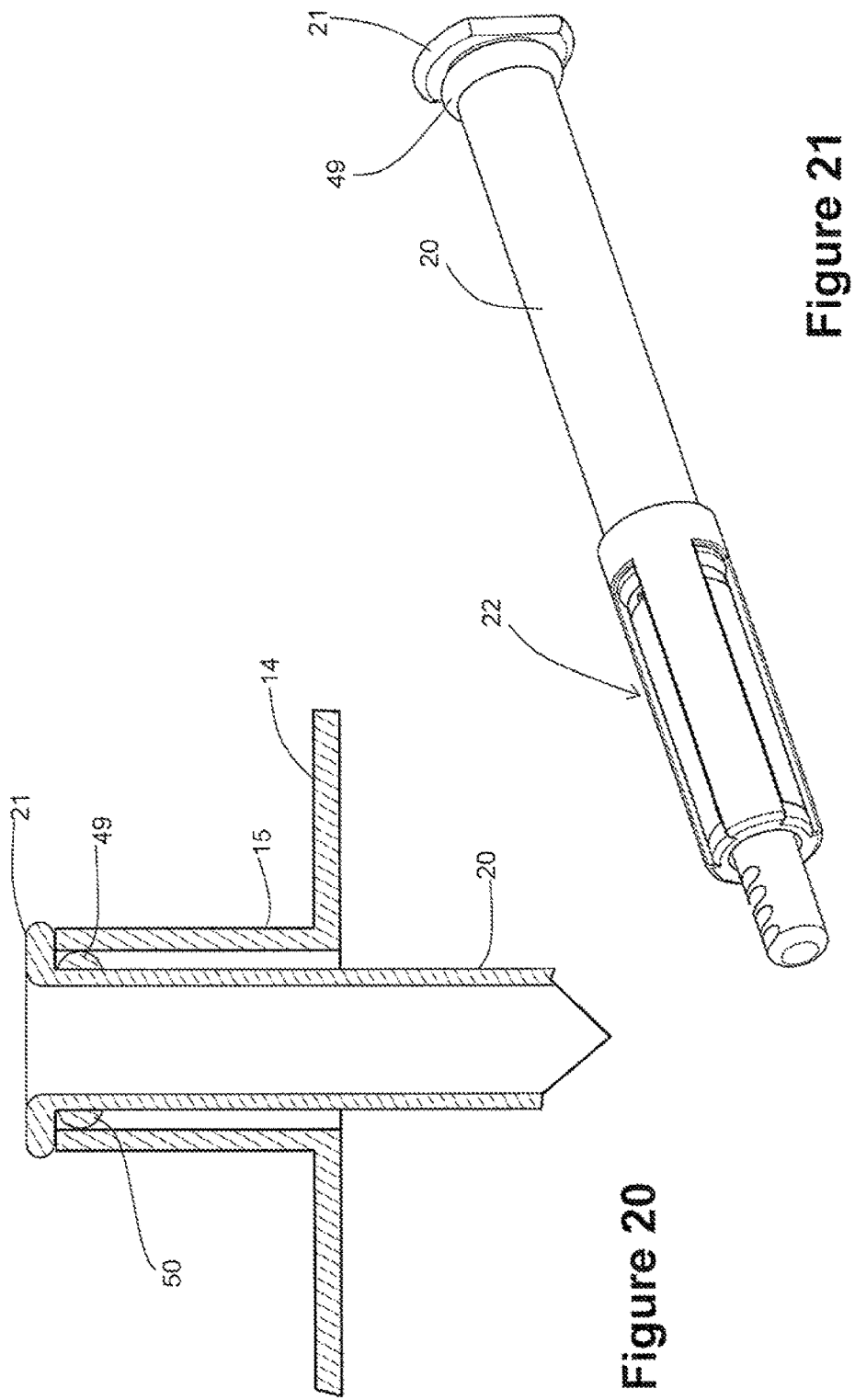

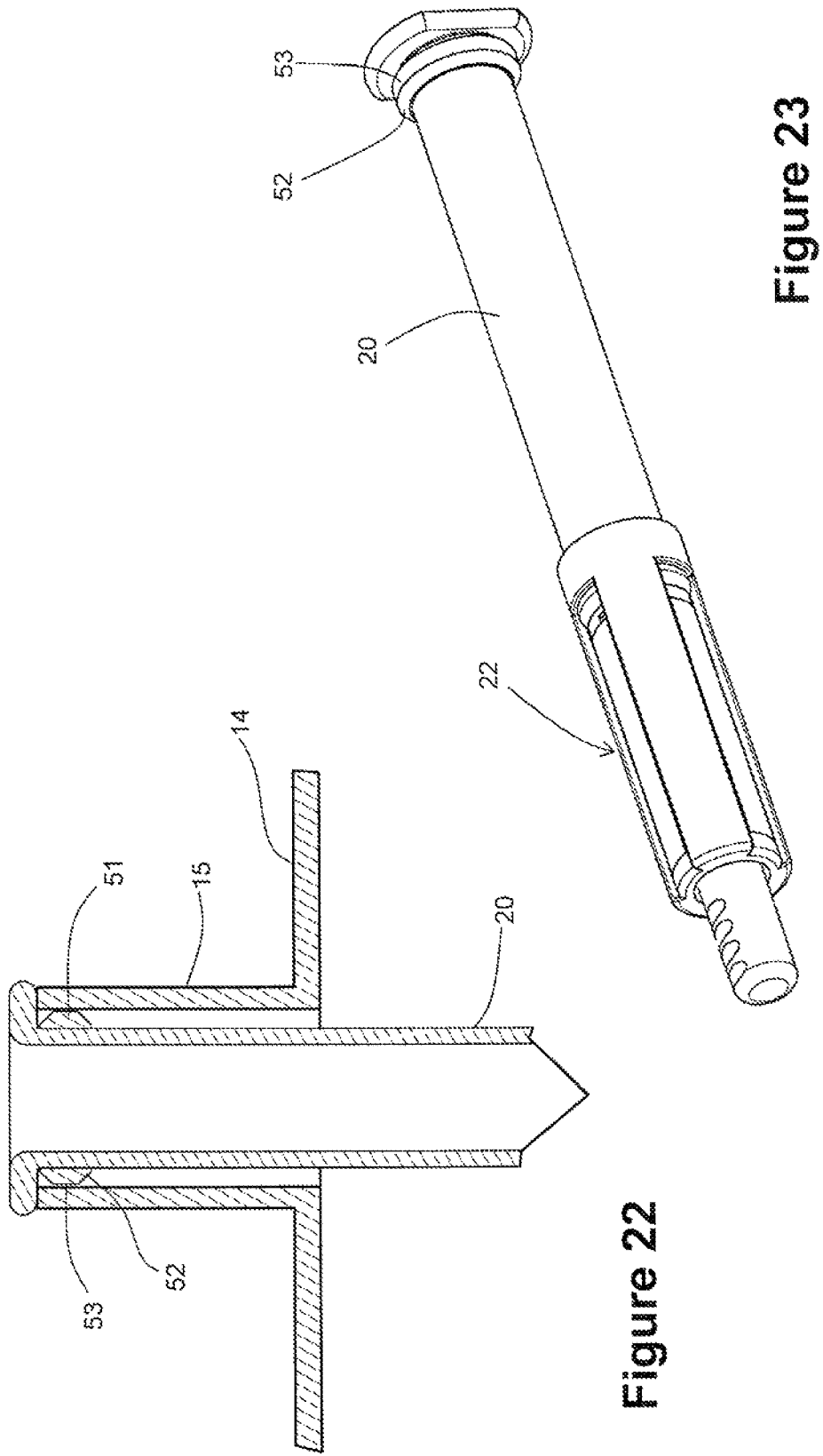

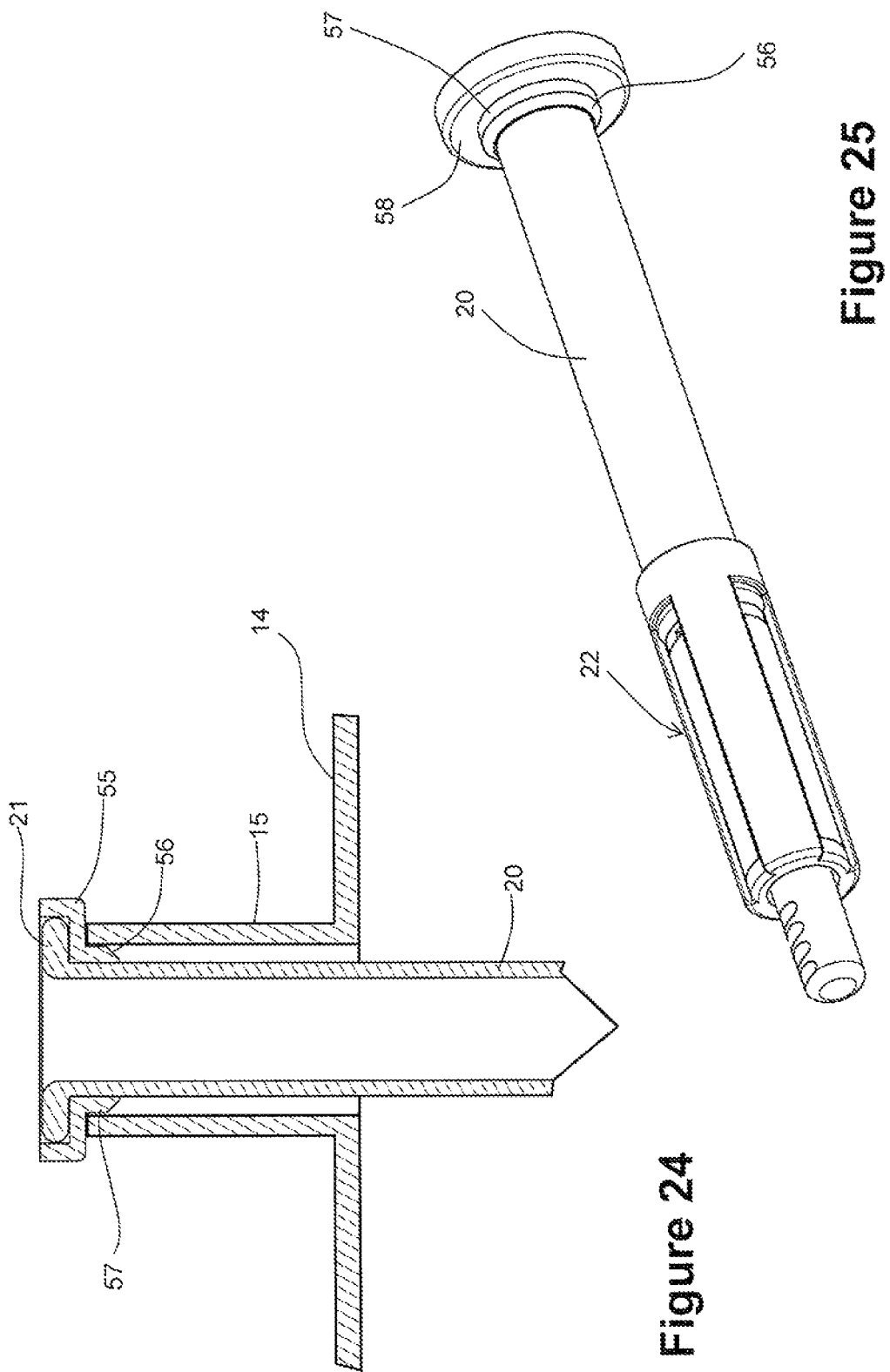

TRAY FOR HANDLING SYRINGE BARRELS

CROSS REFERENCE TO RELATED APPLICATION

The present application is a continuation of U.S. patent application Ser. No. 14/141,183, filed Dec. 26, 2013, which application was published on Apr. 17, 2014, as U.S. Publication No. 2014/0102927, and further which application is a continuation of U.S. patent application Ser. No. 13/634,074, filed Sep. 11, 2012, which application was published on Jan. 3, 2013, as U.S. Publication No. 2013/0001117, and is the U.S. national stage application of International Application PCT/GB2011/050498, filed Mar. 14, 2011, which application was published on Sep. 15, 2011 as International Publication No. WO2011/110872, and claims priority of British Patent Application 1004102.8, filed Mar. 12, 2010, the contents of which are incorporated herein by reference in their entireties.

This invention relates to the combination of a plurality of syringe barrels and a handling system therefor, suitable for use in the course of the manufacture and preparation of syringes pre-filled with a drug for subsequent injection.

A known step in the preparation of pre-filled syringes is the manufacture of a syringe barrel and then the loading of a plurality of those syringe barrels into a so-called tub, for storage and transport purposes to a location where the syringe barrels will be charged with a medicament and fitted with a stopper and a plunger, so permitting the subsequent performance of an injection. The tub has a tray having a plurality of apertures arranged in an array and appropriately sized so that one syringe barrel is closely received in each aperture. The tray is supported in the tub above the base and is a close fit therein so that by accurately positioning the tub in a handling machine, the exact centre of each syringe barrel is known, relative to the tub.

The syringe barrels are prepared under sterile conditions and then are mechanically loaded into a tray supported in a tub, typically with a line of the syringe barrels being picked up and deposited in free apertures in the tray. When the tray is fully loaded, the tub is sealed with a cover and often a plurality of tubs are then packed together, for storage until required for use. When the syringe barrels are to be loaded with a drug, under sterile conditions the syringe barrels are removed from an open tub again by a mechanical handling system which must accurately locate on each syringe barrel, by knowing the precise position of the tub and of the centres of the apertures in the tray supported within the tub.

In the case of a syringe barrel fitted with a staked-in needle, it is the usual practice to fit either a rigid or flexible needle cover to the needle before loading the syringe with a medicament. Such a needle cover also serves to seal the sharp end of the needle and so prevent loss of medicament therethrough. Conveniently, the needle cover is fitted to the syringe barrel before it is loaded into a tub for storage, in order to confer protection to the needle tip.

Current health and safety requirements specify the use of a safe needle device on a syringe in order to guard against accidental needle stick injuries. Though such a device may be fitted to a syringe subsequent to the loading of the syringe with a medicament, since the device may include a needle cover, it would be advantageous for the device to be fitted to the syringe barrel before the loading of the barrel into a tub for storage. Unfortunately, often this is not possible because a safe needle device has a shield which slides rearwardly over the syringe barrel in order to expose the needle; as such, the sleeve must have a larger diameter than that of the syringe barrel.

Such a safe needle device cannot be used with a tray where the syringe barrels closely fit in the apertures in the tray as the safe needle devices will not pass through those apertures. If the apertures are enlarged to allow the safe needle devices to pass therethrough, the syringe barrel will be located only imprecisely in the tray and so there is a high likelihood of mis-handling by a mechanical handling device for lifting the syringe barrels out of the tray. A similar consideration applies in the event that a relatively large shield is to be provided on a syringe barrel to protect a pre-fitted needle, such as may occur with a relatively small diameter syringe body. Further, the same problem may exist with a syringe barrel fitted with a needle having a needle hub secured to the syringe, where the needle hub has a greater diameter than the syringe barrel, and references to the "needle shield" as used hereinafter should be construed broadly to include such a needle hub, a safe needle device or similar component associated with a needle and having a greater diameter than an associated syringe barrel.

It is a principal aim of the present invention to address the above problem and so to allow the fitting of a safe needle device on the forward end of a syringe barrel, before the syringe barrel is carried by a tray of a handling system, while still giving certainty as to the position of the syringe barrel, to allow subsequent reliable mechanical handling.

According to this invention, there is provided a plurality of tubular syringe barrels each having an enlargement at or adjacent one end and a needle shield mounted at the other end thereof wherein the needle shield is of a greater diameter than the syringe barrel, in combination with a handling system for the plurality syringe barrels, the handling system comprising a tray having an array of apertures therethrough each of a sufficient size for a syringe barrel and associated needle shield to pass therethrough and having a support surface configured for engagement by the enlargement of a syringe barrel received in the aperture when the tray is supported generally horizontally and the syringe barrel is lowered into an aperture, at least one of the part of the enlargement adjacent the syringe barrel and said support surface of an aperture having a profile configured to cause substantial concentric alignment of the enlargement within the aperture.

It will be appreciated that a syringe barrel located in an aperture in a tray of a handling system is accurately positioned by virtue of the interengagement of the syringe barrel enlargement with the surface of the tray around the aperture therein receiving the syringe barrel. In this way, the aperture may be sufficiently large to allow a needle shield (i.e. a needle shield fitted to the syringe, a shield of a safe needle device fitted to the syringe or a needle hub) to pass therethrough in a case where the device, hub or shield has a greater diameter than that of the syringe body. Despite this, the interengagement of the enlargement with the support surface of the tray around the aperture causes the syringe barrel to be centred and so coaxial with the aperture such that the exact centre of the syringe barrel is known for handling by a mechanical handling system.

The enlargement of the syringe barrel may be integrally formed with the syringe barrel and so typically may comprise an outwardly projecting flange formed at the rear end of the syringe barrel, to facilitate the performance of an injection with the syringe. Alternatively, the enlargement may be separately formed and then fitted to the syringe barrel, typically adjacent a flange provided at the rear end of the syringe barrel.

In either of these cases, the profile of at least one of the enlargement and the support surface, but preferably both of the enlargement and the support surface, have a reducing cross-section in the downward direction so that interengagement of a part of the enlargement with the support surface centres the syringe barrel to be coaxial with the aperture.

Each aperture in the tray may be provided with a tube surrounding the aperture and projecting from at least one surface (i.e. either the upper surface or the lower surface or possibly both surfaces) of the tray. Most preferably, the tube is in the form of a hollow upstand with said support surface formed at the upper end region of the upstand.

Various embodiments of this invention are envisaged. The surface of the tray around the aperture or the upper end region of the upstand (if provided) may have a generally conical profile of reducing cross-section in the downward direction, with the flange of the syringe barrel co-operating with that conical profile to give the required centring of the syringe body. In the alternative, or possibly in conjunction with this, the region of the junction between the syringe barrel and the flange thereof may be formed to have a generally conical profile of reducing cross-section in the direction towards the other end of the syringe barrel—i.e. the forward end of the syringe barrel, for carrying a needle.

As an alternative to suitably forming the region of the junction between the syringe barrel and the flange, a collar may be positioned on the syringe barrel adjacent the flange, the collar being formed to have a reducing cross-section in the direction towards the other end of the syringe barrel. That reducing cross-section may be provided by a generally conical profile or by the collar having a rounded profile.

As a safe needle device, needle hub or needle shield used in conjunction with a syringe barrel may have a larger diameter than that of the syringe barrel, the underside of at least one of the aperture or the upper end of the upstand (if provided) may be profiled to facilitate removal of the syringe barrel carrying the device, hub or shield from the aperture. For example, where an upstand from the upper surface of the tray is provided, the underside of the junction between the tray and the upstand may be radiused in order to guide into the upstand a needle shield of a greater diameter than the syringe barrel.

In a further embodiment, the support surface may be defined within the upstand by an inwardly directed rib. In this case, the underside of the rib may be chamfered so as to guide the needle shield through the aperture defined by the rib within the upstand.

This invention extends to a combination as described above in conjunction with a cover member for a container carrying a tray and syringe barrels, the cover member being sealingly secured to the free edge of the side wall of the container, remote from the face thereof. The invention further extends to a syringe barrel for use in a combination of this invention as described above and also to a tray for use in such a combination, as described above.

By way of example only, several specific embodiments of this invention will now be described in detail, reference being made to the accompanying drawings in which:—

FIG. 6 shows the first embodiment of a syringe barrel locating in an upstand of the array of apertures in the tray;

FIG. 7 shows the syringe barrel of FIG. 6, when fully centred;

Figure 26:
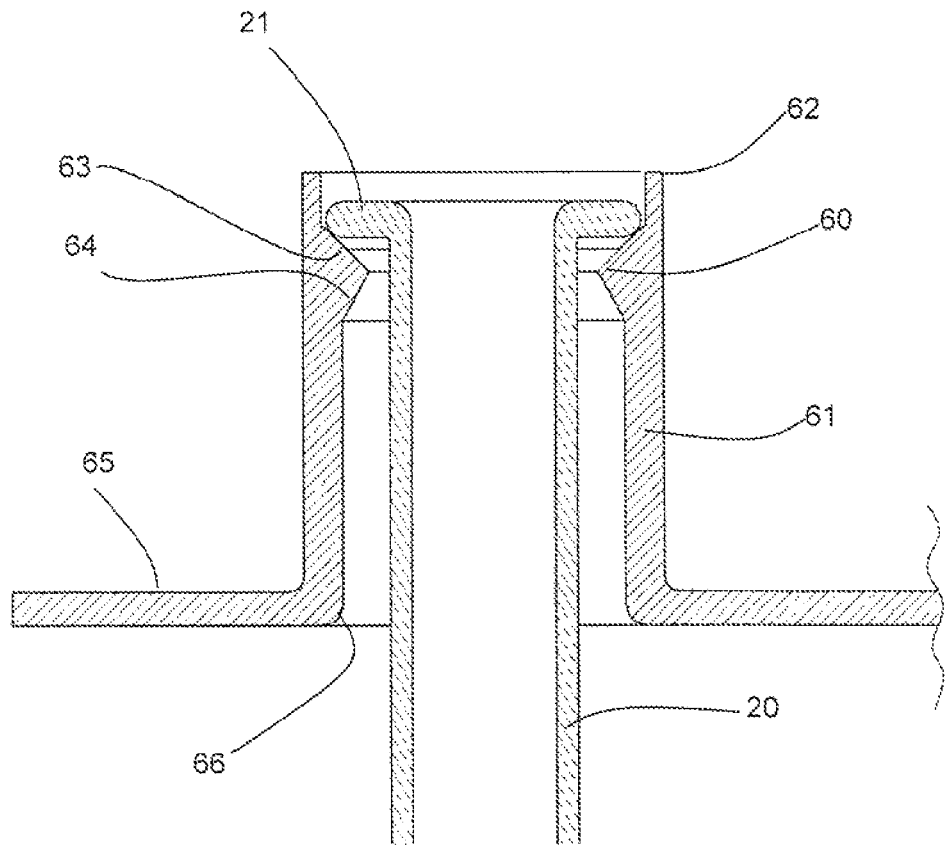

FIGS. 14 and 15 respectively show a cross-section through a fifth embodiment and an isometric view of the syringe barrel and safety needle device of the fifth embodiment;

FIGS. 16 and 17 correspond to FIGS. 14 and 15 but of a sixth embodiment;

FIGS. 18 and 19 correspond to FIGS. 14 and 15 but of a seventh embodiment utilising a collar around the syringe barrel adjacent the flange thereof;

FIGS. 20 and 21, FIGS. 22 and 23 and FIGS. 24 and 25 show eighth, ninth and tenth embodiments each similar to FIGS. 18 and 19 but using different forms of collar; and FIG. 26 shows an eleventh embodiment, similar to the first embodiment of FIGS. 6 to 9.

Figure 1:
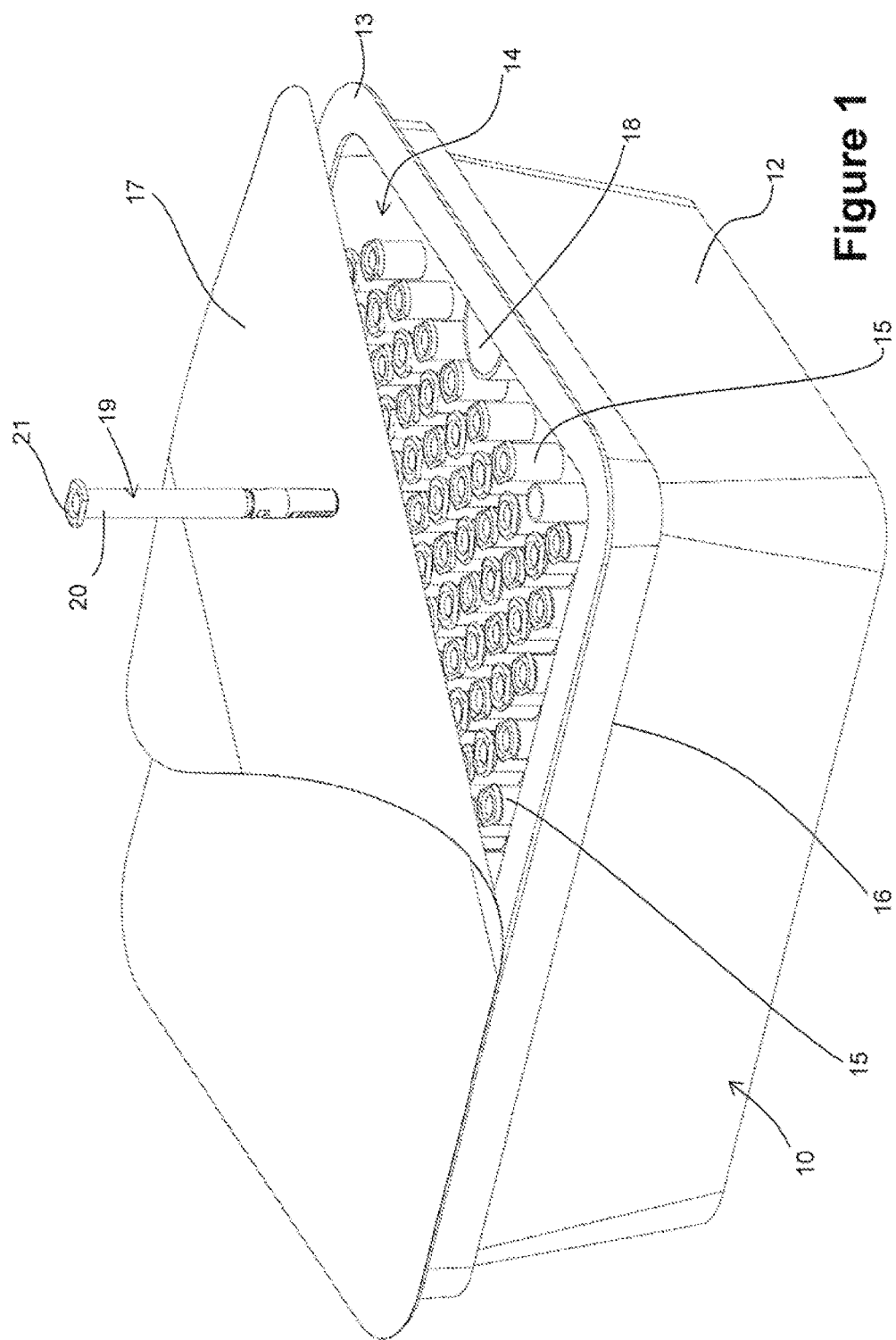
FIG. 1 is an isometric view of a tub carrying a tray of syringe barrels, with one barrel lifted from the tray, for clarity.
Figure 2:
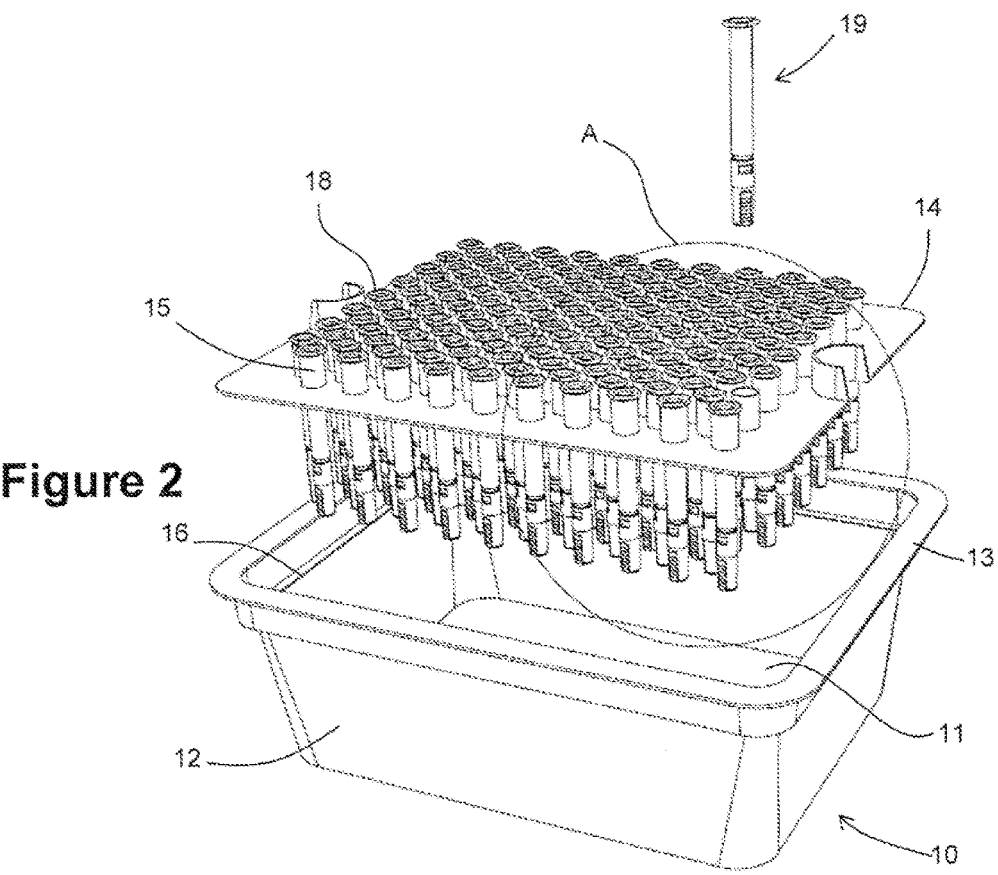
FIG. 2 shows the tub of FIG. 1 with the cover fully removed, the tray of syringe barrels raised from the tub, and one barrel lifted from the tray.
Figure 3:
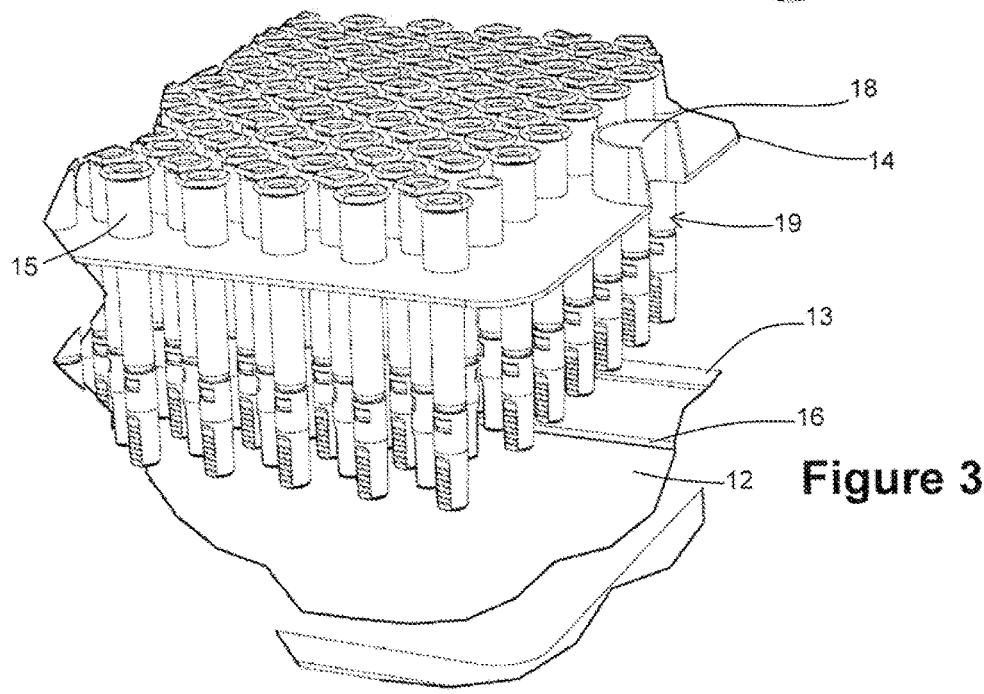
FIG. 3 is a detail view on an enlarged scale of the encircled part marked A on FIG. 2.
Figure 4:
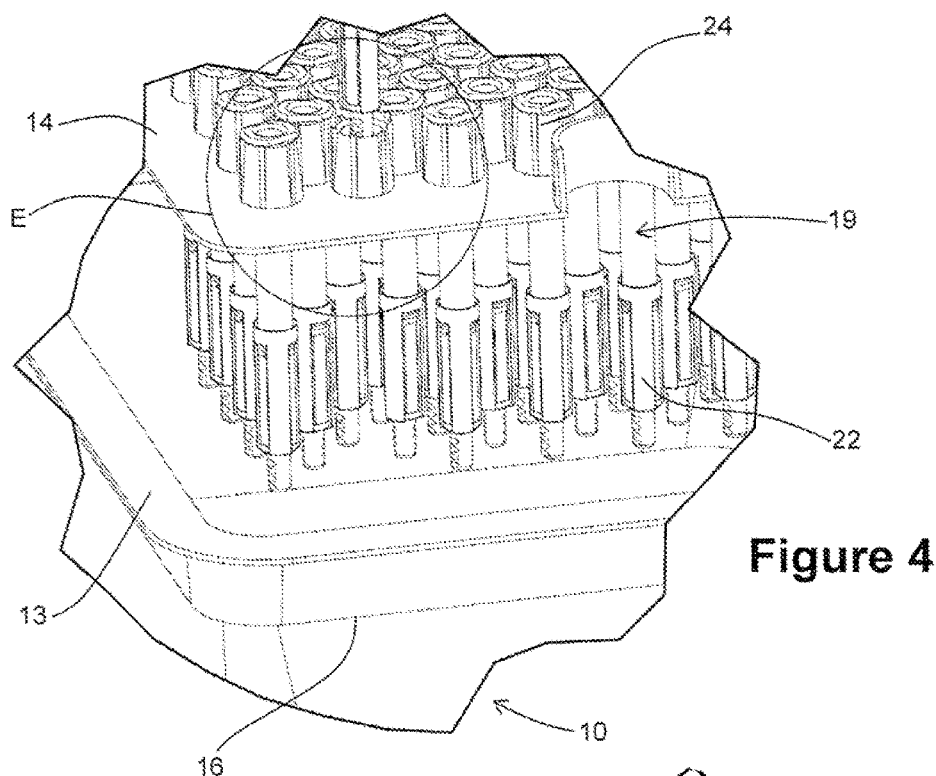
FIG. 4 is a part view on the corner region of the tray of FIGS. 1 to 3 but showing the first embodiment of this invention.

Referring initially to FIGS. 1 to 3, there is shown a syringe handling arrangement as currently employed in the syringe manufacturing art, for the mechanical handling of syringe barrels on a fully automated basis. The known system comprises a tub 10 of generally rectangular cross-sectional shape and comprising a base 11 with an upstanding side wall 12 having an out-turned lip 13 around the upper periphery of the side wall. Disposed within the tub 10 is a tray 14 having a regular array of apertures therein, each aperture having a tubular upstand 15 surrounding the aperture and projecting upwardly from the main surface of the tray. A shoulder 16 is formed around the side wall 12 to support the tray parallel to the base 11 but spaced therefrom. A cover 17 is sealed to the lip 13 in order that the interior of the tub is hermetically sealed from the environment, from manufacture until such time as access is to be gained to the interior of the tub. The tray includes mechanical handling recesses 18 which form no part of this invention.

Syringe barrels 19 of a known form are manufactured separately and are then located within the tub, for storage and transportation to a syringe filling site. Each syringe barrel comprises a cylindrical part 20 having an out-turned flange 21 at the open (rear) end of the barrel. At the forward end, the barrel merges into an integral nose having a through-bore communicating with the interior of the barrel. As manufactured, that nose may be profiled as a connector for the hub of a needle, or a needle may be staked-in to the bore, during manufacture of the syringe barrel. In the case of a staked in needle, a needle cover conventionally is fitted over the needle on to the nose of the syringe. That needle cover may be either flexible or rigid but in either case usually is of a lesser diameter than that of the syringe barrel.

In a conventional arrangement, the syringe barrel is a close fit within an upstand 15, such that the position of each syringe barrel relative to the tray, and hence the tub, is known. Then, by locating the tub carrying the tray on a mechanical handling system, the exact centre of each aperture in the tray and its upstand will be known, both for the insertion of syringe barrels into the tray and subsequently for removal of those syringe barrels. One such mechanical handling system deposits in the tray one complete line of syringe barrels at a time and subsequently when the syringes are to be filled with medicament, another handling system simultaneously lifts a complete line of syringe barrels out of their apertures in the tray.

Sometimes, it is advantageous to fit to the nose of a syringe barrel a safe needle device 22, in order that protection is conferred on the needle both before an injection is performed and subsequent to an injection. Though the latest designs of safe needle device are much more compact than had been proposed previously, nevertheless a safe needle device typically has a larger diameter than that of the syringe barrel with which the device is to be used. This is necessary in order that a protective shield of the safe needle device 22 may slide rearwardly over the barrel, to expose the needle. Also, it may be that a syringe manufacturer may wish to fit a relatively large diameter needle shield to a syringe barrel having a staked-in needle, especially in the case of a small syringe. The needle shield diameter may then be greater than that of the syringe barrel.

The apertures in the tray and the upstands surrounding the apertures of a conventional handling system as described above must be sufficiently large to allow the safe needle device 22 or a shield thereof to pass therethrough, but then a smaller diameter syringe barrel will be a relatively loose fit in the upstand and aperture of the tray, such that the exact position of the syringe barrel axis becomes indeterminate, within a defined range. Subsequent mechanical handling of the syringe barrels may be difficult with a likelihood of dropped syringe barrels on account of an inadequately precise relationship between each syringe barrel and a handling device therefor.

Figure 5:
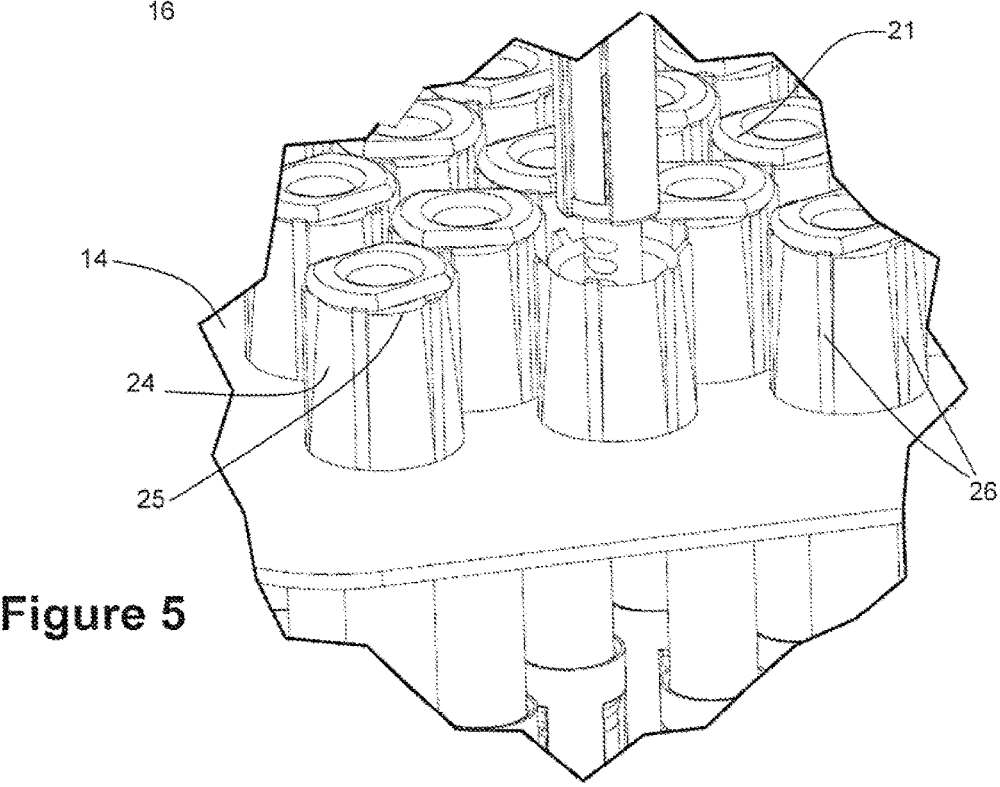
FIG. 5 is a detail view on an enlarged scale of the encircled part marked E on FIG. 4.
Figure 8:
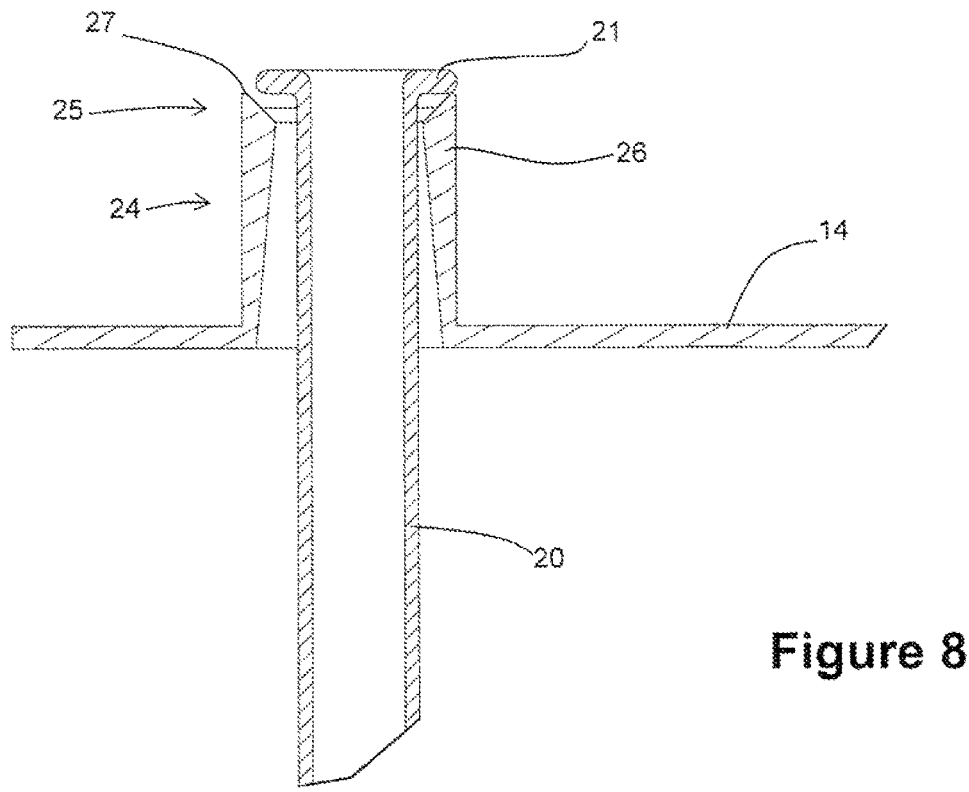
FIG. 8 is a cross-sectional view through the arrangement of FIG. 6.
Figure 9:
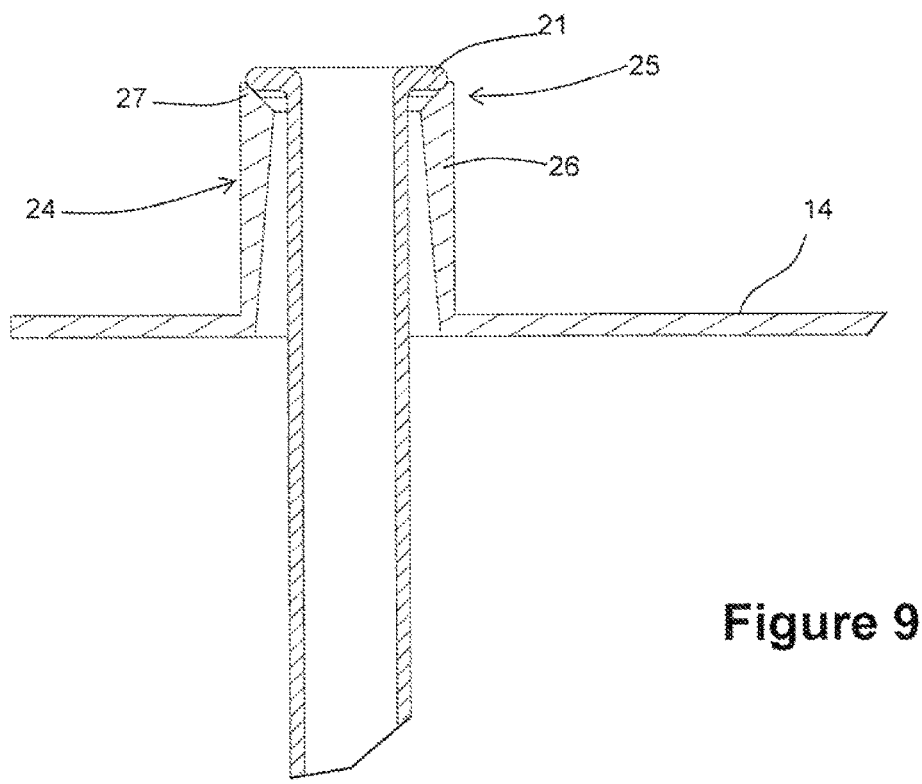
FIG. 9 is a cross-sectional view through the fully centred arrangement of FIG. 7.

In order to address this problem, the measures shown in FIGS. 4 to 9 may be employed, these showing a first embodiment of this invention. In this first embodiment, each upstand 24 has its upper end 25 (i.e. the end of the upstand remote from the tray 14) profiled so as to give a centring function to a syringe barrel 19, by co-operating with the flange 21 of the barrel. In this embodiment, there are six ribs 26 equi-spaced around the upstand 24, each rib extending along the length of the upstand from the tray to the upper end 25. At the upper end, the upstand 24 has a generally conical internal profile 27 tapering in the downward direction and the upper end of each rib 26 has a corresponding surface disposed at the same angle as that of the profile 27, as best seen in FIGS. 5, 8 and 9.

Internally, the diameter of each upstand 24 tapers in the upward direction, with the largest diameter region in the plane of the tray 14, as can be seen in FIGS. 8 and 9. The wall thickness of the upstand is substantially constant except for where the ribs 26 are provided, such that between the ribs, the upstand also has a conical form, with a shallow conical angle.

When a syringe barrel carrying a safe needle device 22 is lowered into an upstand 24, the axis of the barrel might not be coincident with the axis of the upstand as shown in FIGS. 6 and 8, once the safe needle device 22 has passed therethrough. Then, on releasing the syringe from a mechanical handling arrangement, the profile 27 in conjunction with the ribs 26 will co-operate with the flange 21 of the syringe barrel, serving to centre the syringe barrel as shown in FIGS. 7 and 9.

When the syringe barrels are to be removed from the tray, following transport or storage, light vibration or tapping of the tub containing the tray and syringe barrels will cause each barrel to be centred in the associated upstand and aperture, ready for removal by a mechanical handling system. On removal of a barrel, the conical form of each upstand facilitates entry of the larger diameter safe needle device 22 into the lower end of the upstand and so allows for minor misalignment of a barrel with the upstand.

It will be appreciated that with this first embodiment, the syringe barrels 19 are entirely of a known form, and require no modification as compared to a conventional syringe barrel. Equally, the tub 10 is as currently employed in a known syringe handling system and it is only the tray 14 which has been modified to give the required centring functionality when the syringe barrels carry either a safe needle device or a relatively large needle shield at the forward end thereof. Moreover, as the length of a safe needle device or shield will be at least slightly greater than the length of a conventional needle cover, the upstand 15 ensures that the syringe barrel is held above the surface of the tray by a sufficient distance to prevent impact between the forward end of the safe needle device or shield and the base 11 of the tub 10.

Figure 10:
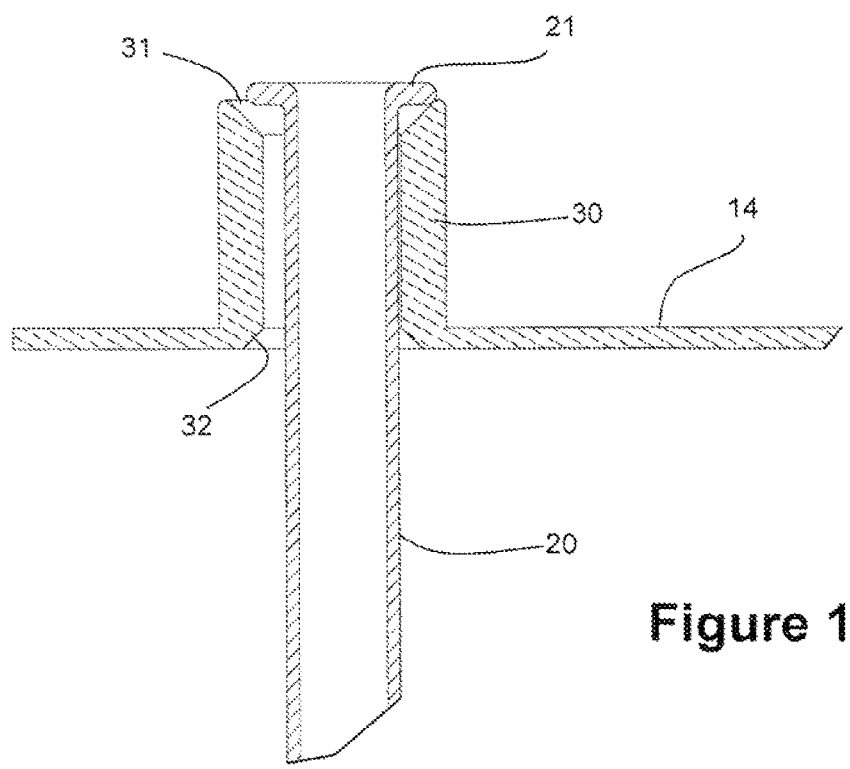
FIGS. 10, 11 and 12 are cross-sectional views through second, third and fourth embodiments.

In the second embodiment shown in FIG. 10, each upstand 30 of the tray 14 has a relatively thick wall and both the upper and lower ends of that wall are given conical profiles 31,32. The conical profile 31 at the upper end of the upstand co-operates with the syringe flange 21 in the same manner as has been described above with reference to FIGS. 4 to 9. The conical profile at the lower end of the upstand facilitates entry of the safe needle device into the upstand, on removing a syringe barrel therefrom.

Figure 11:
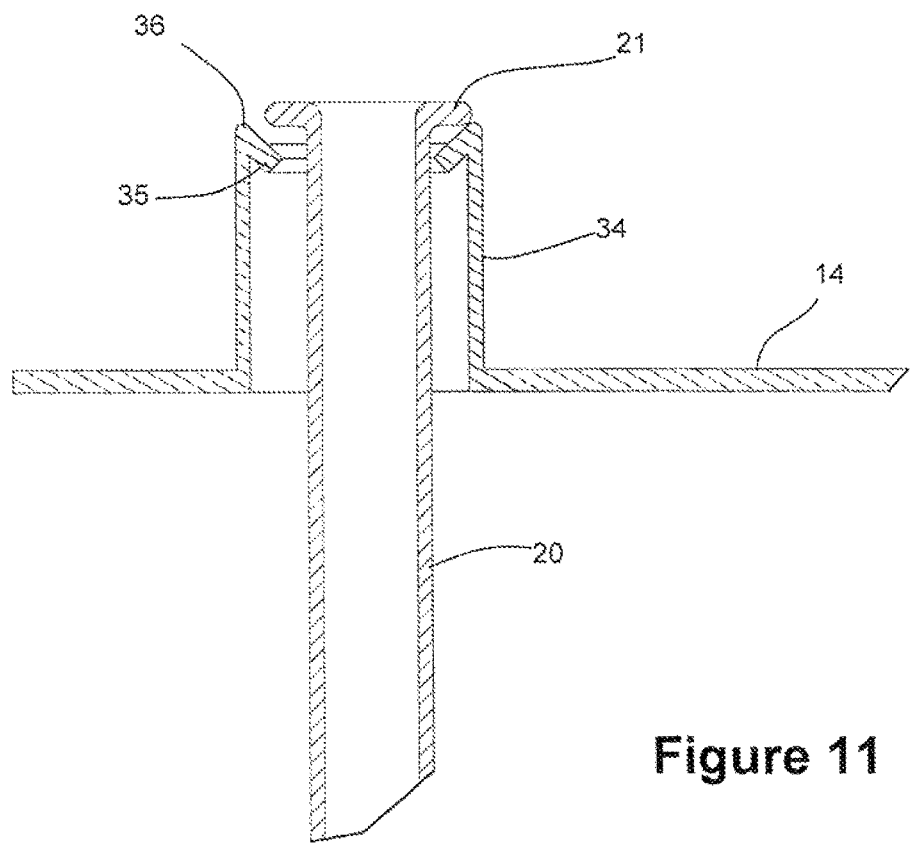

The third embodiment shown in FIG. 11 has a parallel-sided cylindrical upstand 34 provided with an in-turned lip 35 at its upper end. That lip defines a conical profile 36 tapering in the downward direction, to co-operate with the syringe flange 21 thereby to give the centring function.

The embodiments of FIGS. 12 to 17 differ from those described above, in that the syringe barrel has a modified profile in the region of the junction between the syringe barrel and the flange at the rearward end of the barrel. In the case of these embodiments, the upstands from the tray are cylindrical as with the known handling systems but the upstands are of a sufficient diameter (greater than the diameter of the syringe barrel) to allow a safe needle device or large needle shield to pass therethrough.

Figure 12:
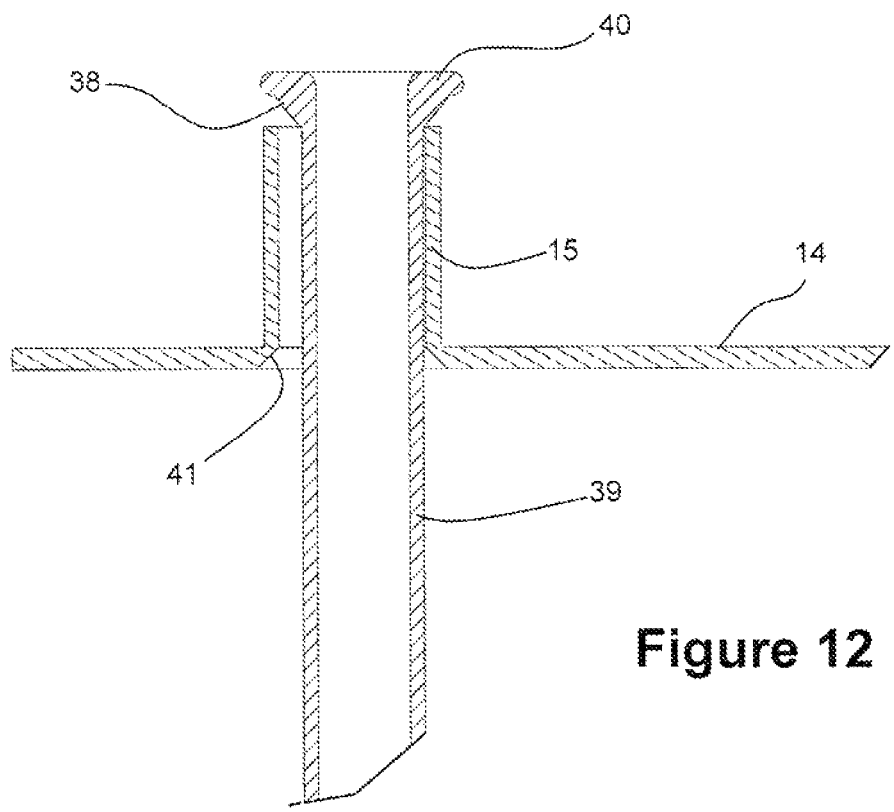
Figure 13:
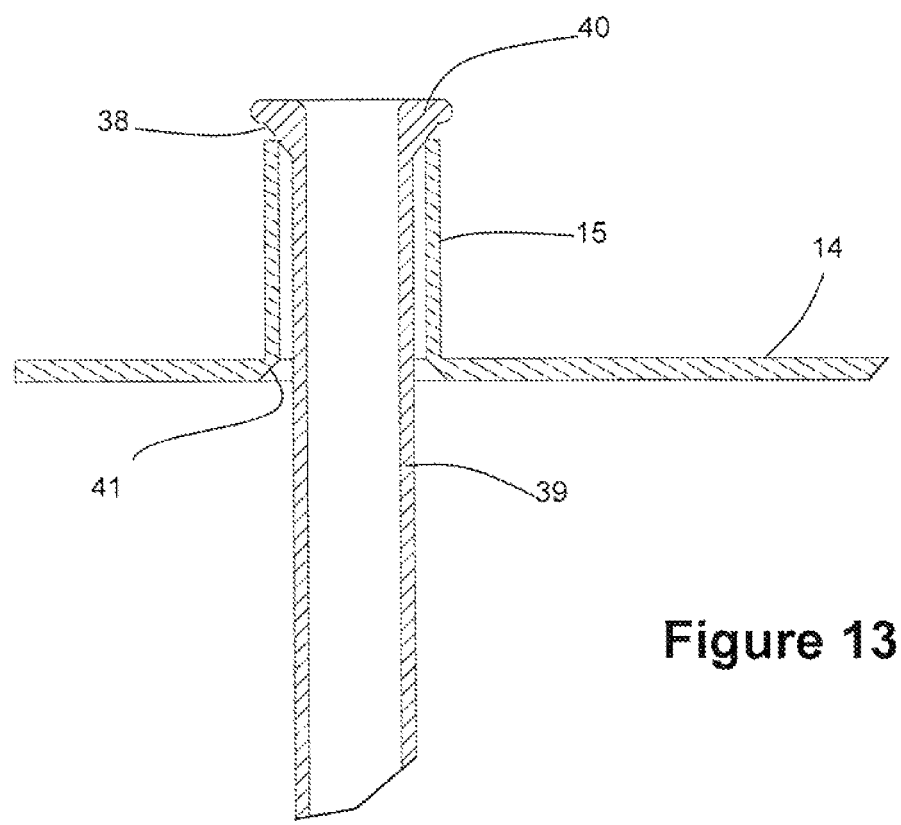
FIG. 13 shows the embodiment of FIG. 12 when fully centred.

In the embodiment of FIGS. 12 and 13, a conical profile 38 is formed in the region of the junction between the syringe barrel 39 and the flange 40. As can be seen from FIGS. 12 and 13 that conical profile serves to correct any axial misalignment between the syringe barrel and the upstand so that the syringe barrel is centred on the upstand. Also shown in FIGS. 12 and 13 is a conical profile 41 at the lower end of the upstand which serves to facilitate entry of the safe needle device into the upstand on removal of a syringe barrel therefrom.

The embodiment of FIGS. 14 and 15 has the same functionality as that described above but the overall profile at the rear end 42 of the syringe barrel is modified such that there is a substantially uniform wall thickness. In all other respects, this embodiment corresponds to that of FIGS. 12 and 13.

The embodiment of FIGS. 16 and 17 also has a substantially uniform wall thickness in the region of the junction between the syringe barrel 43 and a flange 44 at the rear end of the barrel, but the profile defined thereby has a first region 45 of generally conical form and a second region 46 of cylindrical form, of substantially the same diameter as the internal diameter of the upstand. Thus, once the syringe has been centred within the upstand by the co-operation of the first region of the profile with the upstand, the second region of the syringe barrel will enter the upstand and thereafter holds the syringe barrel coaxial with the upstand.

The embodiments of FIGS. 18 to 25 have similar functionality to that of the embodiments of FIGS. 12 to 17 but with a syringe barrel having a conventional form. In the case of these embodiments, a collar is fitted around the syringe barrel 20 to lie closely adjacent the flange 21, the collar having the profiles as shown. The collar 48 of the embodiment of FIGS. 18 and 19 has a simple conical profile and thus corresponds to the embodiment of FIGS. 12 and 13. The embodiment of FIGS. 20 and 21 has a collar 49 of semi-circular cross-section and the part 50 thereof further from the flange 21 serves as a centring profile for the syringe barrel, in the upstand. The collar 51 of the embodiment of FIGS. 22 and 23 has a first part 52 providing a conical surface, a second part 53 providing a cylindrical surface substantially equal in diameter to that of the internal diameter of the upstand and a third part similar to the first part but disposed adjacent the flange 21.

The collars of FIGS. 18 to 23 may be formed of a resilient material such as silicone rubber. This resilience allows precise centring of a syringe barrel and moreover may provide a light frictional grip between a syringe barrel and an upstand. The collars of FIGS. 20 to 23 are symmetrical about a central transverse plane and so may be fitted to a syringe barrel without regard to orientation, so simplifying the assembly process of a collar on a barrel.

The collar 55 shown in FIGS. 24 and 25 is profiled to provide a conical surface 56 giving the centring functionality in association with an upstand, as has been described above. The collar also has a cylindrical surface 57 which is a close fit in the upstand, so that a syringe barrel is held centred when located as shown in FIG. 24. In addition, the collar fits around the flange 21 of the syringe barrel and this provides a radial surface 58 the width of which in the radial direction is comparable to the width of the flange 21. The provision of the collar thus does not lessen the subsequent ease of handling the syringe barrel, for example when performing an injection, as there is still access to a broad flange.

The arrangement shown in FIG. 26 is similar to that of FIGS. 6 to 9 but differs in that an internal rib 60 extends around the inner surface of the upstand 61, below the upper end 62 of that upstand. The rib is defined by substantially conical upper and lower flank surfaces 63,64, the upper flank surface 63 co-operating with the flange 21 of a syringe barrel 19 in order to give a centring function, as has been described above with reference to the previous embodiments. The lower flank surface 64 serves to guide a safe needle device or shield thereof through the rib 60, on removing the syringe barrel from the tray 65. Further, the annular region 66 of the junction between the upstand 61 and the lower surface of the tray is radiused as shown, to facilitate the entry of the safe needle device or shield thereof into the upstand, on removing the syringe barrel from the tray.

In this embodiment, the side wall of the upstand is shown extended axially beyond the rib 60, to give a better location for the flange 21 of a syringe barrel, though it will be appreciated that the rib may be provided at the upper end of the upstand, rather than displaced downwardly by a small distance, as shown in FIG. 26.

The invention claimed is:

1. A combination of a plurality of tubular syringe barrels with a tray of a handling system for use in the course of manufacture and preparation of syringes pre-filled with a drug for subsequent injection, each syringe barrel having a needle and a safe needle device to confer protection on the needle subsequent to an injection; wherein each syringe barrel has a forward end and a rearward end, and an enlargement at or adjacent the rearward end and the needle being fitted to the forward end;

each safe needle device includes a protective shield having a larger diameter than that of the syringe barrel so that rearward sliding movement of the protective shield over the syringe barrel exposes the needle; and the tray has an array of apertures therethrough each of a sufficient size for a syringe barrel and protective shield to pass therethrough, wherein each aperture is provided with a respective tube surrounding the aperture and projecting from the tray, and a support surface is formed at an end region of the tube, and wherein said support surface has a generally conical profile of reducing cross-section in a direction of the tray, whereby interengagement of the enlargement of the syringe barrel with the support surface suspends the syringe barrel through the tube and centers the syringe barrel to be co-axial with the aperture.

2. The combination of claim 1, wherein the enlargement is integrally formed with the syringe barrel and comprises an outwardly projecting flange formed at the rearward end of the syringe barrel.

3. The combination of claim 1, wherein each tube is of substantially circular internal cross-section and of a greater internal diameter than the diameter of the protective shield but of a smaller diameter than the syringe barrel enlargement.

4. The combination of claim 3, wherein each tube has a reducing internal cross-sectional area in the direction away from the tray towards the support surface.

5. The combination of claim 1, wherein a plurality of ribs extend along the external surface of the tube to the support surface thereof.

6. The combination of claim 5, wherein parts of the ribs project beyond the end region of the tube remote from the tray and the support surface is in part defined by the projecting parts of the ribs.

7. The combination of claim 1, wherein said support surface is defined by an in-turned flange formed at the end region of the tube.

8. The combination of claim 1, wherein the enlargement of the syringe barrel is formed to have a generally conical profile of reducing cross-section in the direction towards the forward end of the syringe barrel.

9. The combination of claim 1, wherein the enlargement of the syringe barrel has a first part nearer the rearward end of the barrel of a substantially constant diameter and a second part further from the rearward end of the barrel of a generally conical profile of reducing cross-section in the direction towards the forward end of the barrel.

10. The combination of claim 9, wherein said first part has a diameter which is a close fit in the support surface.

11. The combination of claim 1, wherein a collar is positioned on the barrel, the collar being formed to have a generally conical profile of reducing cross-section in the direction towards the forward end of the syringe barrel.

12. The combination of claim 11, wherein said collar has a first part nearer the rearward end of the barrel of a substantially constant diameter and a second part further from the rearward end of the barrel of a generally conical profile of reducing cross-section in the direction towards the forward end of the syringe barrel.

13. The combination of claim 12, wherein said first part has a diameter which is a close fit in the support surface.

14. The combination of claim 11, wherein the collar is located on the syringe barrel adjacent the enlargement thereof.

15. The combination of claim 1, wherein a collar is positioned on the syringe barrel adjacent the enlargement thereof, the collar being formed to have a rounded external profile of reducing diameter in the direction towards the forward end of the syringe barrel, for at least a part of the axial length of the collar.

16. The combination of claim 1 and in which each aperture has a respective tube upstanding from the tray and having a region remote from the tray, said region being profiled to have a reducing cross-section in the downward direction when the tray is disposed generally horizontally, and at least a part of the enlargement adjacent the syringe barrel or of a collar fitted thereto also is profiled to have a reducing cross-section in the direction towards the forward end of the syringe barrel, whereby the two profiles co-operate to centre the syringe barrel in the aperture.

17. The combination of claim 1, wherein the tray has an underside and at least one of the underside of the aperture and the underside of the support surface is profiled to facilitate removal of the syringe barrel carrying a safe needle device from the tray.

18. The combination of claim 1 and including a tub of rectangular cross-sectional shape and comprising a base with an upstanding side wall having an out-turned lip around the upper periphery of the side wall, the tray being carried and supported generally horizontally above the base of the tub.

19. The combination of claim 18, wherein a cover member is sealingly secured to the out-turned lip of the tub following the loading of the syringes into the apertures of the tray, to enclose the syringes carried by the tray.

20. The combination of claim 1 in conjunction with a tub for the tray and syringe barrels carrying respective safe needle devices, the tub having a base with an upstanding side wall configured to support the tray above the base with clearance between the base and the lower ends of the safe needle devices.

21. The combination of claim 20, wherein the upstanding side wall has a free edge remote from the base and a cover member is provided for the tub, the cover member being sealingly secured to the free edge.

22. A combination of a plurality of tubular syringe barrels with a tray of a handling system for use in the course of manufacture and preparation of syringes pre-filled with a drug for subsequent injection, each syringe barrel having a needle and a safe needle device to confer protection on the needle subsequent to an injection; wherein
    each syringe barrel has a forward end and a rearward end, and an enlargement at or adjacent the rearward end and the needle being fitted to the forward end;
    each safe needle device includes a protective shield having a larger diameter than that of the syringe barrel so that rearward sliding movement of the protective shield over the syringe barrel exposes the needle; and
    the tray has an array of apertures therethrough each of a sufficient size for a syringe barrel and protective shield to pass therethrough, wherein each aperture is provided with a respective tube surrounding the aperture and projecting from the tray, and a support surface is provided at an end region of the tube, and wherein said enlargement is formed to have a generally conical profile of reducing cross-section in a direction toward the forward end of the syringe barrel, whereby interengagement of the enlargement of the syringe barrel with the support surface suspends the syringe barrel through the tube and centers the syringe barrel to be co-axial with the aperture.

23. A combination of a plurality of tubular syringe barrels with a tray of a handling system for use in the course of manufacture and preparation of syringes pre-filled with a drug for subsequent injection, each syringe barrel having a needle and a safe needle device to confer protection on the needle subsequent to an injection; wherein
    each syringe barrel has a forward end and a rearward end, and an enlargement at or adjacent the rearward end and the needle being fitted to the forward end, wherein said enlargement of said syringe barrel has a first part nearer the rearward end of the barrel of a substantially constant diameter and a second part further from the rearward end of the barrel of a generally conical profile of reducing cross-section in a direction toward the forward end of the barrel;
    each safe needle device includes a protective shield having a larger diameter than that of the syringe barrel so that rearward sliding movement of the protective shield over the syringe barrel exposes the needle; and
    the tray has an array of apertures therethrough each of a sufficient size for a syringe barrel and protective shield to pass therethrough, wherein each aperture is provided with a respective tube surrounding the aperture and projecting from the tray, and a support surface is provided at an end region of the tube, whereby interengagement of the enlargement of the syringe barrel with the support surface suspends the syringe barrel through the tube and centers the syringe barrel to be co-axial with the aperture.

\* \* \* \* \*